United States Patent [19]

Sasakawa et al.

[11] Patent Number: 4,880,786
[45] Date of Patent: Nov. 14, 1989

[54] ADDITIVE SOLUTION FOR BLOOD PRESERVATION AND ACTIVATION

[75] Inventors: Shigeru Sasakawa; Masayuki Shiba, both of Tokyo, Japan

[73] Assignees: Ube Industries, Ltd., Ube; Showa Denko K.K.; The Japanese Red Cross Society, both of Tokyo, all of Japan

[21] Appl. No.: 142,786

[22] Filed: Jan. 11, 1988

[30] Foreign Application Priority Data

Jan. 14, 1987 [JP] Japan .................................. 62-5080

[51] Int. Cl.⁴ ........................ A01N 1/02; A61K 35/14
[52] U.S. Cl. .......................................... 514/53; 435/2; 424/101
[58] Field of Search ............... 435/2; 514/53; 424/101

[56] References Cited

U.S. PATENT DOCUMENTS 4,769,318 9/1988 Hamasaki et al. .................. 424/101

Primary Examiner—Ronald W. Griffin
Assistant Examiner—Everett White
Attorney, Agent, or Firm—Frishauf, Holtz, Goodman & Woodward

[57] ABSTRACT

There is disclosed an additive solution for blood preservation and activation, which comprises a phosphoenolpyruvic acid represented by the following formula (I):

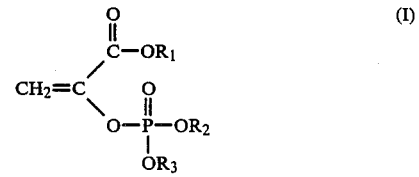

wherein $R_1$ represents a hydrogen atom or an alkyl group having 1 to 12 carbon atoms, $R_2$ and $R_3$ represent a hydrogen atom, an alkali metal or an alkyl group having 1 to 12 carbon atoms, respectively, an L-ascorbic acid-phosphate or its pharmaceutically acceptable salt, a saccharide, adenine and a pharmaceutically acceptable organic buffer.

11 Claims, No Drawings

ADDITIVE SOLUTION FOR BLOOD PRESERVATION AND ACTIVATION

BACKGROUND OF THE INVENTION

This invention relates to an additive solution for blood preservation and activation.

In our country, heretofore, a blood preservative comprising sodium citrate, citric acid and glucose (abbreviated as "ACD" solution) or a blood preservative comprising sodium citrate, citric acid, glucose and sodium dihydrogen phosphate dihydrate (generally abbreviated as "CPD" solution) has been used for preservation of collected blood. On the other hand, in Europe and the United States of America, a blood preservative comprising sodium citrate, citric acid, glucose, sodium dihydrogen phosphate dihydrate and adenine (generally abbreviated as "CPD-A" solution) has been used.

However, even when blood is preserved by use of the blood preservative as described above, there ensue the following problems:

(1) the shape of erythrocyte changes during preservation;

(2) the oxygen releasing ability of hemoglobin in erythrocytes decreases during storage;

(3) hemolysis occurs excessively in erythrocytes with high hematocrit value (abbreviated as "Ht value") [more specifically, Ht indicates the corporeal components in blood (erythrocyte, platelet and leukocyte) as represented by $$Ht = \frac{\text{corporeal components}}{\text{whole blood}} \times 100, \text{ and}$$

most of the corporeal components are erythrocytes. And, erythrocyte concentrates under the present situation have Ht values of 70 to 80%, and the blood preservatives under the present situation have been said to be unsuitable for preservation of erythrocyte concentrates with high Ht values of over 80%. Normal human Ht values are said to be 36 to 48% for men and 34 to 42% for women].

Such problems are becoming extremely important in recent years as the demand for platelet, leukocyte and plasmapoor erythrocyte concentrate increases. In other words, while an increase in separation ratio of plasma, platelets, leukocytes, etc. from the collected blood to obtain a high Ht value may have the advantage in increasing the amount of plasma fractionation products and alleviating troubles during transfusion (for example, side effects accompanied with leukocytes such as pyrexia, antibody production, etc.), enhancement of separation of plasma, platelets, leukocytes, etc., other than erythrocytes from the collected blood will result in such problems as mentioned above, that is the oxygen releasing ability of erythrocytes is further reduced, the shape of the erythrocyte changes and hemolysis occurs excessively.

SUMMARY OF THE INVENTION

Accordingly, an object of the present invention is to provide an additive solution for blood preservation and activation which is effective for prevention of change in shape of erythrocytes, reduction of oxygen releasing ability of erythrocytes and hemolysis in a preserved blood, particularly erythrocyte concentrates.

The present inventors have studied intensively on cell membrane permeability and energy metabolism of erythrocytes and consequently found an effective additive solution which is effective for functional activation of erythrocytes and also effective for strengthening cell membrane to accomplish the present invention.

More specifically, the present invention concerns an additive solution for blood preservation and activation, comprising a phosphoenolpyruvic acid represented by the following formula (I):

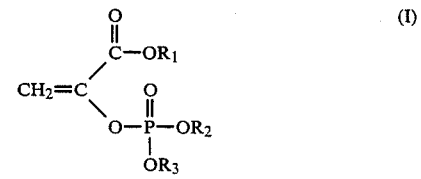

wherein $R_1$ represents a hydrogen atom or an alkyl group having 1 to 12 carbon atoms, $R_2$ and $R_3$ represent a hydrogen atom, an alkali metal or an alkyl group having 1 to 12 carbon atoms, respectively, an L-ascorbic acid-phosphate or its pharmaceutically acceptable salt, a saccharide, adenine and a pharmaceutically acceptable organic buffer.

DESCRIPTION OF THE PREFERRED EMBODIMENTS

In the phosphoenolpyruvic acid represented by the formula (I), when $R_1$, $R_2$ or $R_3$ is an alkyl group having 1 to 12 carbon atoms, it may specifically be a methyl group, an ethyl group, an n-propyl group, an isopropyl group, an n-butyl group, an isobutyl group, a sec-butyl group, a tert-butyl group, an n-amyl group, an isoamyl group, a sec-amyl group, an active amyl group, a tert-amyl group, an n-hexyl group, an n-heptyl group, an n-octyl group, an n-nonyl group, an n-decyl group, an n-undecyl group, an n-dodecyl group or the like.

When $R_2$ and $R_3$ are alkali metals, they may be specifically sodium or potassium, etc.

However, since phosphoenolpyruvic acid is usually available as sodium phosphoenolpyruvate hydrate, it is preferable to use a sodium salt hydrate.

As the L-ascorbic acid-phosphoric acid ester (hereinafter called "AP") to be used in the present invention, there may be included pharmaceutically acceptable phosphates such as L-ascorbic acid-2-phosphate represented by the following formula (II):

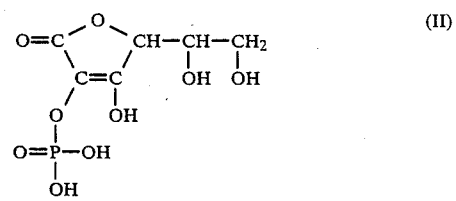

and L-ascorbic acid-3-phosphate represented by the following formula (III):

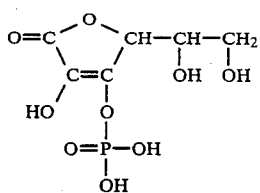

As the pharmaceutically acceptable salt of AP, there may be included, for example, sodium salt, magnesium salt, potassium salt, calcium salt, etc.

In the present invention, specific examples of the saccharide may include disaccharides such as maltose, sucrose and the like and monosaccharides such as galactose, mannitol and the like.

Further, in the present invention, pharmaceutically acceptable organic buffers may be used, and preferably organic salts known to exhibit no strong toxicity in living bodies or exist in living bodies may be included. More specifically, for example, sodium citrate, sodium acetate, sodium pyruvate, sodium lactate, sodium tartarate, etc. may be employed. These organic buffers are preferred, because they can function as a buffer for pH control and also have the action of inhibiting formation of fibrin which causes blood clotting.

In the additive solution for blood preservation and activation of the present invention, in addition to the respective components as described above, an organic acid may be also added, preferred examples thereof may include organic acids which are known to exhibit no strong toxicity in living bodies or exist in living bodies. More specifically, for example, citric acid, acetic acid, pyruvic acid, lactic acid, tartaric acid, etc. can be employed. These organic acids are preferred, because they can function as a buffer for pH control and also have the action of inhibiting formation of fibrin which causes blood clotting.

The additive solution for blood preservation and activation of the present invention should preferably be used in the form of a solution. For example, in an additive solution containing monosodium phosphoenolpyruvate; AP sodium salt or AP magnesium salt; maltose, mannitol or sucrose; adenine; and trisodium citrate, it is preferred that 10 to 100 mmole/liter of monosodium phosphoenolpyruvate, 5 to 100 mmole/liter of sodium L-ascorbatephosphate or magnesium L-ascorbatephosphate, 40 to 200 mmole/liter maltose, mannitol or sucrose, 0.1 to 5 mmole/liter of adenine and 1 to 50 mmole/liter of trisodium citrate is contained and the osmolarity is adjusted with sodium chloride (280 to 350 mOsm/kg). More preferably, it contains 15 to 50 mmole/liter of monosodium phosphoenolpyruvate, 5 to 50 mmole/liter of sodium L-ascorbatephosphate or magnesium L-ascorbatephosphate, 50 to 150 mmole/liter of maltose, mannitol or sucrose, 0.2 to 2 mmole/liter of adenine and 5 to 20 mmole/liter of trisodium citrate and the osmolarity is adjusted with sodium chloride (280 to 350 mOsm/kg). Otherwise, it is particularly preferred to add phosphoric acid or its alkali metal salt such as sodium dihydrogen phosphate, preferably in an amount of 1 to 20 mmole/liter.

When using the above prepared solution, it is preferably added in an amount of 10 to 150 ml per 100 ml of the collected blood.

In the additive solution for blood preservation and activation of the present invention, the phosphoenolpyruvic acid represented by the above formula (I) permeates through the cell membranes of erythrocytes and produces 2,3-diphosphoglycerate (abbreviated as "2,3-DPG") and adenosine triphosphate (abbreviated as "ATP") through the glycolytic metabolism in erythrocytes. The 2,3-DPG plays a role in controlling oxygen affinity of erythrocytes, and prevents reduction of oxygen releasing ability of erythrocytes during blood preservation. Adenine also permeates through the cell membrane of erythrocytes and produces ATP in erythrocytes. The ATP thus formed within cells contributes to phosphorylation of cell membrane, maintenance of erythrocyte shape and survival of erythrocytes in vivo and/or in vitro. On the other hand, the saccharide contributes to strengthen cell membrane of erythrocytes and maintains the structure of erythrocytes to prevent hemolysis. Further, the organic acid and pharmaceutically acceptable organic buffer play a role in discharging carbon dioxide in erythrocytes and maintaining acid-base equilibrium associated therewith during preservation of blood. Particularly, when containing sodium citrate, it will not permeate through the cell membranes of erythrocytes, but has buffering action to be effective for maintaining pH and is also effective in inhibiting fibrin formation which causes aggregation of erythrocytes to occur.

EXAMPLES

The present invention is described in more detail below by referring to Examples and Test examples.

EXAMPLE 1

Composition of an additive solution for blood preservation and activation

One liter of an aqueous solution (pH 6.5) was made up by dissolving 46.8 g (130 mmole) of maltose, 0.94 g (6 mmole) of sodium dihydrogen phosphate dihydrate, 0.135 g (1 mmole) of adenine, 8.32 g (40 mmole) of monosodium phosphoenolpyruvate monohydrate, 5.64 g (15 mmole) of sodium L-ascorbate-2-phosphate and 1.76 g (6 mmole) of trisodium citrate in water.

EXAMPLE 2

Composition of an additive solution for blood preservation and activation

One liter of an aqueous solution (pH 6.5) was made up by dissolving 46.8 g (130 mmole) of maltose, 0.94 g (6 mmole) of sodium dihydrogen phosphate dihydrate, 0.068 g (0.5 mmole) of adenine, 6.24 g (30 mmole) of monosodium phosphoenolpyruvate monohydrate, 5.69 g (15 mmole) of magnesium L-ascorbate-2-phosphate and 2.94 g (10 mmole) of trisodium citrate in water.

EXAMPLE 3

Composition of an additive solution for blood preservation and activation

One liter of an aqueous solution (pH 6.5) was made up by dissolving 46.8 g (130 mmole) of maltose, 0.068 g (0.5 mmole) of adenine, 6.24 g (30 mmole) of monosodium phosphoenolpyruvate monohydrate, 5.69 g (15 mmole) of magnesium L-ascorbate-2-phosphate and 2.94 g (10 mmole) of trisodium citrate in water.

TEST EXAMPLE

(1) Preparation of erythrocyte concentrate

Human peripheral blood was collected in a blood bag and centrifuged to separate leukocytes, platelets and plasma, etc. therefrom, thus obtaining an erythrocyte concentrate with a hematocrit (Ht) value of 90 to 95%.

(2) Changes with lapse of time when stored at 4° to 6° C.

To 150 ml of the erythrocyte concentrate obtained in (1) was added 150 ml of the additive solution prepared in Example 1. The mixture was stored at 4° to 6° C., and sampling was practised every one week, and 2,3-DPG and ATP in erythrocytes and hemoglobin amounts in supernatant were measured. The results are shown in Table 1.

TABLE 1

| Storage period (week) | Components of erythrocyte | | Hb[a] (mg/100 ml of supernatant) |
|---|---|---|---|
| | 2,3-DPG (μmole/gHb) | ATP (μmole/gHb) | |
| 0 | 12.1 | 4.9 | 1.8 |
| 1 | 14.3 | 5.0 | 10 |
| 2 | 14.5 | 4.9 | 14 |
| 3 | 13.7 | 4.9 | 25 |
| 4 | 10.4 | 4.5 | 34 |
| 5 | 8.6 | 4.0 | 45 |
| 6 | 6.3 | 3.5 | 56 |

[a]Indicating the extent of hemolysis, and hemolysis is more severe as the value is greater.

Thus, by addition of the additive solution prepared in Example 1 to the erythrocyte concentrate, 2,3-DPG and ATP in the stored blood can be maintained over a long term to make it clear that no remarkable hemolysis of blood cells has occurred during this period. Particularly, 2,3-DPG is found to be increased as compared with before initiation of preservation after 1 to 3 weeks.

(3) Changes with storage period when stored at 4° C. and incubated at 37° C. for 30 minutes before measurement The same experiment as in (2) was introduced except that the mixture of the erythrocytes concentrate obtained in (1) and the additive solution prepared in Example 1 was incubated before measurement at 37° C. for 30 minutes. The results are shown in Table 2.

TABLE 2

| Storage period (week) | Components of erythrocyte | | Hb[a] (mg/100 ml of supernatant) |
|---|---|---|---|
| | 2,3-DPG (μmole/gHb) | ATP (μmole/gHb) | |
| 0 | 15.5 | 6.2 | 1.8 |
| 1 | 18.6 | 6.0 | 9.5 |
| 2 | 17.4 | 5.8 | 15 |
| 3 | 16.4 | 5.6 | 25 |
| 4 | 12.5 | 5.4 | 33 |
| 5 | 11.0 | 4.8 | 45 |
| 6 | 7.5 | 4.0 | 55 |

[a]Indicating the extent of hemolysis, and hemolysis is more severe as the value is greater.

When incubation-treatment at 37° C. is carried out immediately before transfusion, improvements to great extent can be seen in both 2,3-DPG and ATP values, thus exhibiting clearly the effect of addition of sodium phosphoenolpyruvate and sodium L-ascorbate-2-phosphate.

(4) Changes with storage period when the additive solution prepared in Example 2 is used The same tests as in (2) and (3) were conducted except for adding 150 ml of the additive solution prepared in Example 2 to 150 ml of the erythrocyte concentrate obtained in (1). Otherwise, incubation was performed at 37° C. for 60 minutes. The results are shown in Table 3 and Table 4.

TABLE 3

| Storage period (week) | Stored at 4 to 6° C. | | |
|---|---|---|---|
| | Components of erythrocyte | | Hb[a] (mg/100 ml of supernatant) |
| | 2,3-DPG (μmole/gHb) | ATP (μmole/gHb) | |
| 0 | 12.6 | 5.1 | 1.6 |
| 1 | 19.1 | 5.0 | 2.8 |
| 2 | 19.7 | 5.0 | 7.0 |
| 3 | 16.4 | 4.9 | 13.4 |
| 4 | 13.7 | 4.7 | 14.0 |
| 5 | 10.9 | 4.2 | 22.9 |
| 6 | 8.9 | 3.7 | 31.1 |

TABLE 4

| Storage period (week) | Incubated at 37° C. for 60 minutes | | |
|---|---|---|---|
| | Components of erythrocyte | | Hb[a] (mg/100 ml of supernatant) |
| | 2,3-DPG (μmole/gHb) | ATP (μmole/gHb) | |
| 0 | 25.5 | 6.8 | 4.4 |
| 1 | 22.2 | 6.3 | 3.2 |
| 2 | 21.9 | 6.0 | 7.0 |
| 3 | 17.9 | 5.9 | 11.7 |
| 4 | 14.8 | 5.7 | 14.6 |
| 5 | 12.6 | 5.2 | 24.0 |
| 6 | 10.8 | 5.0 | 32.7 |

[a]Indicating the extent of hemolysis, and hemolysis is more severe as the value is greater.

Also after 6 weeks, activity of the stored erythrocytes was found to be maintained at an extremely high level. 2,3-DPG and ATP are at the same levels as the fresh blood, thus indicating clearly usefulness of the present preservative.

(5) Changes with storage period when the additive solution prepared in Example 3 is used The same tests as in (2) and (3) were conducted except for adding 150 ml of the composition solution prepared in Example 3 to 150 ml of the erythrocyte concentrate obtained in (1). Otherwise, incubation was performed at 37° C. for 60 minutes. The results are shown in Table 5 and Table 6.

TABLE 5

| Storage period (week) | Stored at 4 to 6° C. | | |
|---|---|---|---|
| | Components of erythrocyte | | Hb[a] (mg/100 ml of supernatant) |
| | 2,3-DPG (μmole/gHb) | ATP (μmole/gHb) | |
| 0 | 8.7 | 5.2 | 5.1 |
| 1 | 11.7 | 4.4 | 6.3 |
| 2 | 10.2 | 4.3 | 6.5 |
| 3 | 8.7 | 3.5 | 9.4 |
| 4 | 7.5 | 3.8 | 16.7 |
| 5 | 4.6 | 2.4 | 25.8 |
| 6 | 2.6 | 1.8 | 45.9 |

TABLE 6

| Storage period (week) | Incubated at 37° C. for 60 minutes | | Hb[a] (mg/100 ml of supernatant) |
|---|---|---|---|
| | Components of erythrocyte | | |
| | 2,3-DPG (μmole/gHb) | ATP (μmole/gHb) | |
| 0 | 16.8 | 5.7 | 6.7 |
| 1 | 12.7 | 4.9 | 6.9 |
| 2 | 12.1 | 5.0 | 9.4 |
| 3 | 9.3 | 4.6 | 11.2 |
| 4 | 8.8 | 4.5 | 17.8 |
| 5 | 6.2 | 3.4 | 36.0 |
| 6 | 3.3 | 3.0 | 40.7 |

[a]Indicating the extent of hemolysis, and hemolysis is more severe as the value is greater.

It has been found that, in erythrocytes concentrate, the concentrations of 2,3-DPG and ATP within erythrocytes are higher than in fresh blood on initiation of preservation and are maintained at the level equal to that of fresh blood even after 6 weeks, and also with very little hemolysis, whereby activity of erythrocytes after preservation can be maintained at an extremely high level.

With the additive solution for blood preservation and activation of the present invention, it is possible to preserve the blood with maintenance of activities of erythrocytes for a long period in a collected blood, particularly applied to erythrocyte concentrate having high Ht value.

We claim:

1. An additive solution for blood preservation and activation, comprising a phosphoenolpyruvic acid represented by the following formula (I):

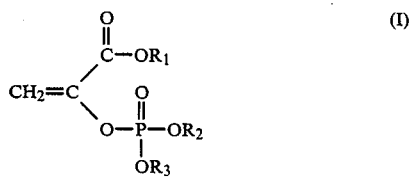

wherein $R_1$ represents a hydrogen atom or an alkyl group having 1 to 12 carbon atoms, $R_2$ and $R_3$ represent a hydrogen atom, an alkali metal or an alkyl group having 1 to 12 carbon atoms, respectively,
an L-ascorbic acid-phosphate or its pharmaceutically acceptable salt, a saccharide, adenine and a pharmaceutically acceptable organic buffer.

2. The additive solution for blood preservation and activation according to claim 1, wherein said L-ascorbic acid-phosphate or its pharmaceutically acceptable salt is L-ascorbic acid-2-phosphate represented by the following formula (II):

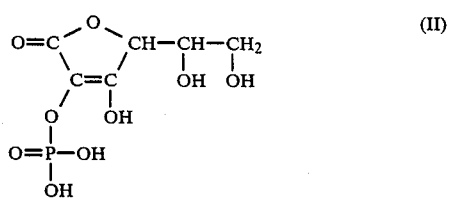

or L-ascorbic acid-3-phosphate represented by the following formula (III):

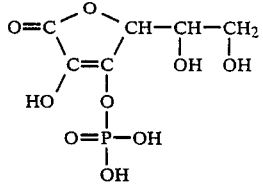

and sodium salt, magnesium salt, potassium salt or calcium salt of the above.

3. The additive solution for blood preservation and activation according to claim 2, wherein said L-ascorbic acid-phosphate or its pharmaceutically acceptable salt is sodium L-ascorbatephosphate.

4. The additive solution for blood preservation and activation according to claim 1, wherein said saccharide is maltose, sucrose, galactose or mannitol.

5. The additive solution for blood preservation and activation according to claim 1, wherein said pharmaceutically acceptable organic buffer is sodium citrate.

6. The additive solution for blood preservation and activation according to claim 1, comprising an aqueous solution containing 10 to 100 mmole/liter of monosodium phosphoenolpyruvate, 5 to 100 mmole/liter of sodium L-ascorbatephosphate or magnesium L-ascorbatephosphate, 40 to 200 mmole/liter of maltose, mannitol or sucrose, 0.1 to 5 mmole/liter of adenine and 1 to 50 mmole/liter of trisodium citrate and also containing sodium chloride added to adjust the osmolarity of suspension medium, as necessary.

7. The additive solution for blood preservation and activation according to claim 6, comprising an aqueous solution containing 10 to 100 mmole/liter of monosodium phosphoenolpyruvate, 5 to 100 mmole/liter of sodium L-ascorbatephosphate, 40 to 200 mmole/liter of maltose, mannitol or sucrose, 0.1 to 5 mmole/liter of adenine and 1 to 50 mmole/liter of trisodium citrate and also containing sodium chloride added to adjust the osmolarity of suspension medium, as necessary.

8. The additive solution for blood preservation and activation according to claim 6, comprising an aqueous solution containing 10 to 100 mmole/liter of monosodium phosphoenolpyruvate, 5 to 100 mmole/liter of magnesium L-ascorbatephosphate, 40 to 200 mmole/liter of maltose, mannitol or sucrose, 0.1 to 5 mmole/liter of adenine and 1 to 50 mmole/liter of trisodium citrate and also containing sodium chloride added to adjust the osmolarity of suspension medium, as necessary.

9. The additive solution for blood preservation and activation according to claim 6, said solution further comprises 1 to 20 mmole/liter of phosphoric acid or its alkali metal salt.

10. The additive solution for blood preservation and activation according to claim 6, wherein said aqueous solution containing 15 to 50 mmole/liter of monosodium phosphoenolpyruvate, 5 to 50 mmole/liter of sodium L-ascorbatephosphate or magnesium L-ascorbatephosphate, 50 to 150 mmole/liter of maltose, mannitol or sucrose, 0.2 to 2 mmole/liter of adenine and 5 to 20 mmole/liter of trisodium citrate and also containing sodium chloride added to adjust the osmolarity of suspension medium, as necessary.

11. The additive solution for blood preservation and activation according to claim 10, said solution further comprises 1 to 20 mmole/liter of phosphoric acid or its alkali metal salt.

* * * * *